(12) United States Patent
Ishitsuka et al.

(10) Patent No.: US 10,959,705 B2
(45) Date of Patent: Mar. 30, 2021

(54) ULTRASONIC PROBE AND ULTRASONIC DIAGNOSTIC DEVICE

(71) Applicant: Toshiba Medical Systems Corporation, Otawara (JP)

(72) Inventors: Masaaki Ishitsuka, Nasushiobara (JP); Hiroyuki Shikata, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 877 days.

(21) Appl. No.: 15/083,609

(22) Filed: Mar. 29, 2016

(65) Prior Publication Data

US 2016/0287213 A1 Oct. 6, 2016

(30) Foreign Application Priority Data

Mar. 30, 2015 (JP) ............................. JP2015-070308

(51) Int. Cl.
| | |
|---|---|
| *A61B 8/00* | (2006.01) |
| *G01S 15/89* | (2006.01) |
| *A61B 8/14* | (2006.01) |
| *A61B 8/08* | (2006.01) |
| *G01S 7/52* | (2006.01) |

(52) U.S. Cl.
CPC .......... *A61B 8/5207* (2013.01); *A61B 8/4444* (2013.01); *A61B 8/54* (2013.01); *G01S 7/5208* (2013.01); *G01S 15/8927* (2013.01); *A61B 8/14* (2013.01); *A61B 8/461* (2013.01)

(58) Field of Classification Search
CPC ....... A61B 8/5207; A61B 8/4444; A61B 8/54; A61B 8/14; A61B 8/461; G01S 15/8927; G01S 7/5208
See application file for complete search history.

(56) References Cited

U.S. PATENT DOCUMENTS

| | | | | |
|---|---|---|---|---|
| 4,070,905 A | * | 1/1978 | Kossoff | G01N 29/0609 367/104 |
| 6,352,510 B1 | * | 3/2002 | Barabash | A61B 8/145 128/916 |
| 6,537,219 B2 | | 3/2003 | Poland et al. | |
| 6,582,367 B1 | * | 6/2003 | Robinson | A61B 8/14 600/443 |
| 2002/0145941 A1 | * | 10/2002 | Poland | G01S 7/52034 367/11 |

(Continued)

FOREIGN PATENT DOCUMENTS

| | | |
|---|---|---|
| JP | 2003-325507 A | 11/2003 |
| JP | 2004-527325 A | 9/2004 |

(Continued)

*Primary Examiner* — Boniface N Nganga
(74) *Attorney, Agent, or Firm* — Oblon, McClelland, Maier & Neustadt, L.L.P.

(57) ABSTRACT

An ultrasonic probe according to an embodiment includes a group of transducer elements and a plurality of electronic circuits. The group of transducer elements constitutes a main array that is divided into a plurality of sub-arrays, and is two-dimensionally arranged. The electronic circuits are arranged corresponding to the arrangement of the transducer elements constituting the sub-array. At least one of the electronic circuits is a first electronic circuit having a first function. At least one of the electronic circuits is a second electronic circuit having a second function different from the first function.

19 Claims, 8 Drawing Sheets

(56) References Cited

U.S. PATENT DOCUMENTS

| | | | | |
|---|---|---|---|---|
| 2006/0119223 | A1* | 6/2006 | Ossmann | A61B 8/4281 310/334 |
| 2007/0016023 | A1* | 1/2007 | Phelps | G01S 7/52023 600/437 |
| 2007/0167814 | A1* | 7/2007 | Wakabayashi | A61B 8/12 600/459 |
| 2008/0221454 | A1* | 9/2008 | Davidsen | A61B 8/483 600/459 |
| 2008/0262351 | A1* | 10/2008 | Scampini | G01S 7/52079 600/443 |
| 2011/0172537 | A1* | 7/2011 | Hongou | A61B 8/00 600/447 |
| 2011/0237953 | A1* | 9/2011 | Olsson | G01S 7/5208 600/459 |
| 2011/0301467 | A1* | 12/2011 | Miller | G01S 15/8913 600/459 |
| 2013/0079641 | A1* | 3/2013 | Zwirn | A61B 5/0095 600/447 |
| 2013/0324853 | A1* | 12/2013 | Matsuda | G10K 11/18 600/459 |
| 2014/0139072 | A1* | 5/2014 | Sudol | H01L 41/0475 310/334 |

FOREIGN PATENT DOCUMENTS

| | | | | |
|---|---|---|---|---|
| JP | 2005270423 A | * | 10/2005 | |
| JP | 2005-304692 A | | 11/2005 | |
| WO | WO-2006035384 A1 | * | 4/2006 | G01S 7/52079 |

\* cited by examiner

ULTRASONIC PROBE AND ULTRASONIC DIAGNOSTIC DEVICE

CROSS-REFERENCE TO RELATED APPLICATIONS

This application is based upon and claims the benefit of priority from Japanese Patent Application No. 2015-070308, filed on Mar. 30, 2015; the entire contents of which are incorporated herein by reference.

FIELD

An embodiment described herein relates generally to an ultrasonic probe and an ultrasonic diagnostic device.

BACKGROUND

Developed are ultrasonic diagnostic devices that generate an ultrasonic image obtained by imaging an internal state of a subject using, as an ultrasonic probe, a two dimensional array probe (2D array probe) including a plurality of transducer elements arranged in a lateral direction and an elevation direction.

DETAILED DESCRIPTION

The following describes an embodiment an ultrasonic probe and an ultrasonic diagnostic device in detail with reference to the attached drawings.

Embodiment

Figure 1:
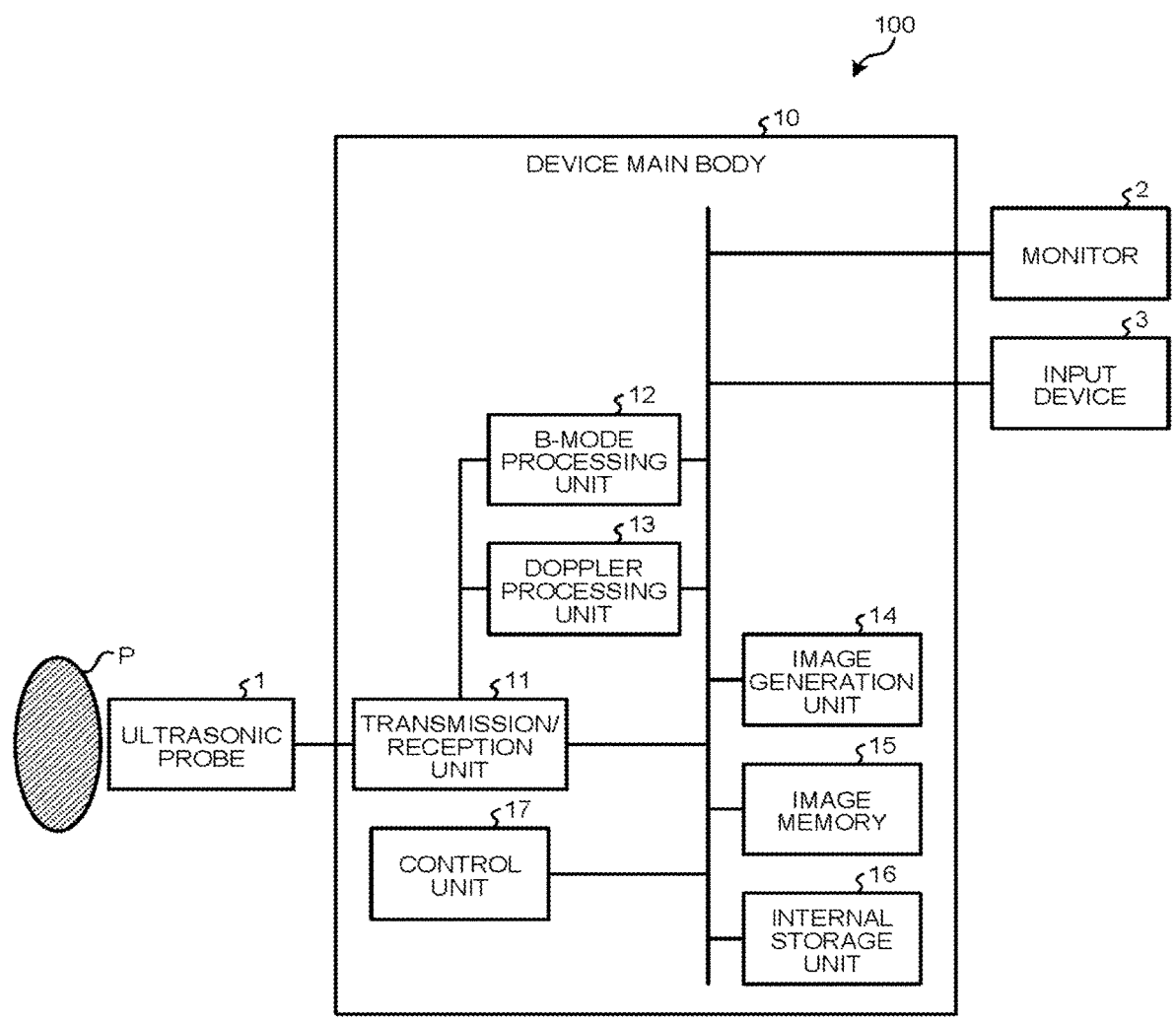
FIG. 1 is a diagram for explaining a configuration example of an ultrasonic diagnostic device according to an embodiment.

First, the following describes a configuration example of the ultrasonic diagnostic device to which the ultrasonic probe according to the embodiment is applied. FIG. 1 is a diagram for explaining a configuration example of an ultrasonic diagnostic device 100 according to the embodiment. As illustrated in FIG. 1, the ultrasonic diagnostic device 100 according to the embodiment includes an ultrasonic probe 1, a monitor 2, an input device 3, and a device main body 10.

The ultrasonic probe 1 includes a plurality of transducer elements that transmit ultrasonic waves and receive reflected waves. The transducer elements are two-dimensionally arranged. Each of the transducer elements generates ultrasonic waves based on a drive signal supplied from a transmission circuit 22 (described later) via a transmission/reception switch 21 (described later). Each of the transducer elements receives an echo (reflected wave) from a subject P, and converts the received echo into an echo signal (reflected wave signal) that is an electric signal. The ultrasonic probe 1 also includes an acoustic matching layer provided to the transducer element, a rear load member (backing material) that suppresses propagation of ultrasonic waves from the transducer element toward the rear, and other components. The ultrasonic probe 1 is detachably connected to the device main body 10. The type of the ultrasonic probe 1 may be a convex type or a sector type, and various types of ultrasonic probes can be used as the ultrasonic probe 1.

For example, when the ultrasonic waves are transmitted from the ultrasonic probe 1 to the subject P, the transmitted ultrasonic waves are successively reflected by a discontinuous surface of acoustic impedance in body tissues of the subject P, and received as echoes by the transducer elements included in the ultrasonic probe 1. Each echo is converted into an echo signal by the transducer element that has received the echo. Amplitude of the echo signal depends on a difference in the acoustic impedance on the discontinuous surface by which the ultrasonic waves are reflected. In a case in which transmitted ultrasonic pulses are reflected by moving blood flow or a surface such as a cardiac wall, the echo signal is subjected to frequency shift depending on a velocity component of a moving object in an ultrasonic wave transmitting direction due to the Doppler effect.

The monitor 2 displays a graphical user interface (GUI) through which an operator of the ultrasonic diagnostic device 100 inputs various setting requests using the input device 3, or displays an ultrasonic image and other items generated in the device main body 10. The monitor 2 is an example of a display unit.

The input device 3 includes a trackball, a switch, a dial, a touch command screen, a foot switch, a joystick, and other components. The input device 3 receives various setting requests from the operator of the ultrasonic diagnostic device 100, and transfers the received various setting requests to the device main body 10. For example, the input device 3 receives various setting requests for controlling the ultrasonic probe 1, and transfers the received various setting requests to a control unit 17.

The device main body 10 is a device that controls transmission and reception of the ultrasonic waves by the ultrasonic probe 1, and generates an ultrasonic image based on the echo signal corresponding to the echo received by the ultrasonic probe 1. As illustrated in FIG. 1, the device main body 10 includes a transmission/reception unit 11, a B-mode processing unit 12, a Doppler processing unit 13, an image generation unit 14, an image memory 15, an internal storage unit 16, and the control unit 17.

The transmission/reception unit 11 includes a pulser circuit and other components. The pulser circuit repeatedly generates a rate pulse for forming transmission ultrasonic waves at a predetermined rate frequency (pulse repetition frequency (PRF)), and outputs the generated rate pulse as a drive signal for driving transducer elements 20c (described later) to the ultrasonic probe 1.

The transmission/reception unit 11 also includes an A/D converter and a reception beam former. When the transmission/reception unit 11 receives the echo signal output from the ultrasonic probe 1, first, the A/D converter converts the echo signal into digital data, the reception beam former generates echo data by performing phasing addition processing on the digital data from respective channels, and transmits the genera d echo data to the B-mode processing unit 12 and the Doppler processing unit 13.

The transmission/reception unit 11 is controlled by the control unit 17 to output an amplitude value of the drive signal output from each of transmission circuits 22 (described later) to a control circuit 28 (described later). The transmission/reception unit 11 is controlled by the control unit 17 to output a delay amount of the drive signal and a delay amount of the echo signal corresponding to each of the delay circuits 23 (described later). The transmission/reception unit 11 is controlled by the control unit 17 to output an identifier for indentifying a function in which a gain corresponds to an elapsed time used for time gain control in each of time gain controllers 25 (described later).

The B-mode processing unit 12 receives the echo data output from the transmission/reception unit 11, and performs, for example, logarithmic amplification, envelope detection processing on the received echo data to generate data (B-mode data) in which signal intensity is represented by luminance.

The Doppler processing unit 13 receives the echo data output from the transmission/reception unit 11, performs frequency analysis on velocity information from the received echo data, extracts e ho components of blood flow, tissues, and a contrast medium due to the Doppler effect, and generates data (Doppler data) obtained by extracting moving object information such as an average velocity, distribution, and power for multiple points.

The image generation unit 14 generates an ultrasonic image from the data generated by the B-mode processing unit 12 and the Doppler processing unit 13. That is, the image generation unit 14 generates a B-mode image in which the intensity of the echo is represented by the luminance from the B-mode data generated by the B-mode processing unit 12. The image generation unit 14 also generates, from the Doppler data generated by the Doppler processing unit 13, an average velocity image, a distribution image, and a power image that represent the moving object information, or a color Doppler image as a combination thereof. That is, the image generation unit 14 generates the ultrasonic image based on the output from the ultrasonic probe 1. The image generation unit 14 is, for example, implemented with a processor. The processor means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)).

The image memory 15 is a memory that stores the ultrasonic image generated by the image generation unit 14. The image memory 15 can also store the data generated by the B-mode processing unit 12 or the Doppler processing unit 13.

The internal storage unit 16 stores a control program for transmitting or receiving the ultrasonic waves and performing image processing and display processing, diagnostic information (for example, a patient ID and findings of a doctor), a diagnostic protocol, and various pieces of data such as various body marks. The internal storage unit 16 is also used to keep the image stored by the image memory 15 as needed.

The control unit 17 is a control processor (CPU) that implements a function as an information processing device (calculator), and controls the entire processing of the ultrasonic diagnostic device 100. Specifically, the control unit 17 controls the processing performed by the transmission/reception unit 11, the B-mode processing unit 12, the Doppler processing unit 13, and the image generation unit 14 based on the various setting requests input by the operator via the input device 3 or various control programs and various pieces of data read from the internal storage unit 16. The control unit 17 also performs control to cause the monitor 2 to display the ultrasonic image stored by the image memory 15, various images stored by the internal storage unit 16, a graphical user interface (GUI) for directing the processing of the image generation unit 14, a processing result obtained by the image generation unit 14, and other items.

The control unit 17 also controls the transmission/reception unit 11 to output the amplitude value of the drive signal output from each of the transmission circuits 22 (described later) to the control circuit 28 (described later). The control unit 17 also control the transmission/reception unit 11 to output the delay amount of the drive signal and the delay amount of the echo signal corresponding to each of the delay circuits 23 (described later) to the control circuit 28 (described later). The control unit 17 also controls the transmission/reception unit 11 to output, to the control circuit 28 (described later), the identifier for indentifying the function in which the gain corresponds to the elapsed time used for time gain control in each of the time gain controllers 25 (described later).

Figure 2:
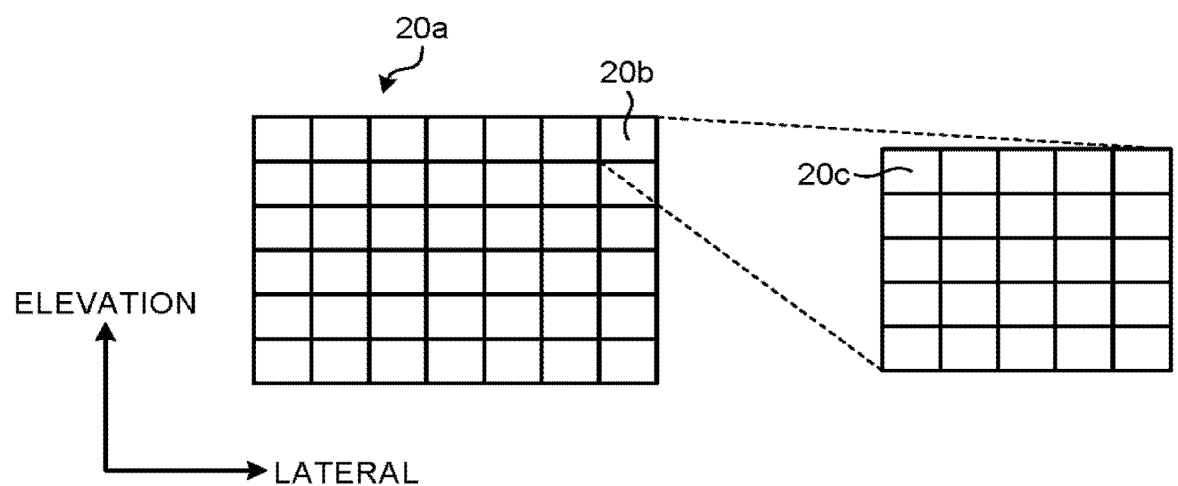
FIG. 2 is a diagram for explaining an example of an arrangement of a group of transducer elements.

Next, with reference to FIG. 2, the following describes an example of an arrangement of a group of transducer elements included in the ultrasonic probe 1 connected to the device main body 10 in the embodiment. FIG. 2 is a diagram for explaining an example of the arrangement of the group of transducer elements.

As illustrated in the example of FIG. 2, the ultrasonic probe 1 is a 2D array probe. That is, as illustrated in the example of FIG. 2, the group of transducer elements included in the ultrasonic probe 1 constitutes a main array 20a. The main array 20a is divided into a plurality of sub-arrays 20b in a lateral direction and an elevation direction. The sub-array 20b represents, in a case in which a plurality of transducer elements 20c constituting the group of transducer element are separated into a group of predetermined number of the transducer elements 20c, an arrangement of the transducer elements 20c belonging to the separated group. The following describes a case in which the sub-arrays 20b are two-dimensionally arranged. In the example of FIG. 2, the sub-array 20b represents, in a case in which the transducer elements 20c constituting the group of transducer elements are separated into a group of twenty-five transducer elements 20c, the arrangement of the twenty-five transducer elements 20c belonging to the separated group. In the example of FIG. 2, a reference numeral "20b" is given to only one sub-array, and the reference numeral "20b" is not given to the other sub-arrays. Similarly, in the example of FIG. 2, the reference numeral "20c" given to only one transducer element, and the reference numeral "20c" is not given to the other transducer elements.

The sub-array 20b is constituted of a plurality of transducer elements 20c that are two-dimensionally arranged in the lateral direction and the elevation direction. In the example of FIG. 2, the sub-array 20b represents the arrangement of twenty-five transducer elements 20c arranged as follows: five in the lateral direction and five in the elevation direction. That is, the sub-array 20b illustrated in the example of FIG. 2 is constituted of a plurality of transducer elements 20c arranged in a grid of "5×5". In other words, the sub-array 20b illustrated in the example of FIG. 2 is constituted of a plurality of transducer elements 20c arranged in a grid of "odd number×odd number".

Figure 3:
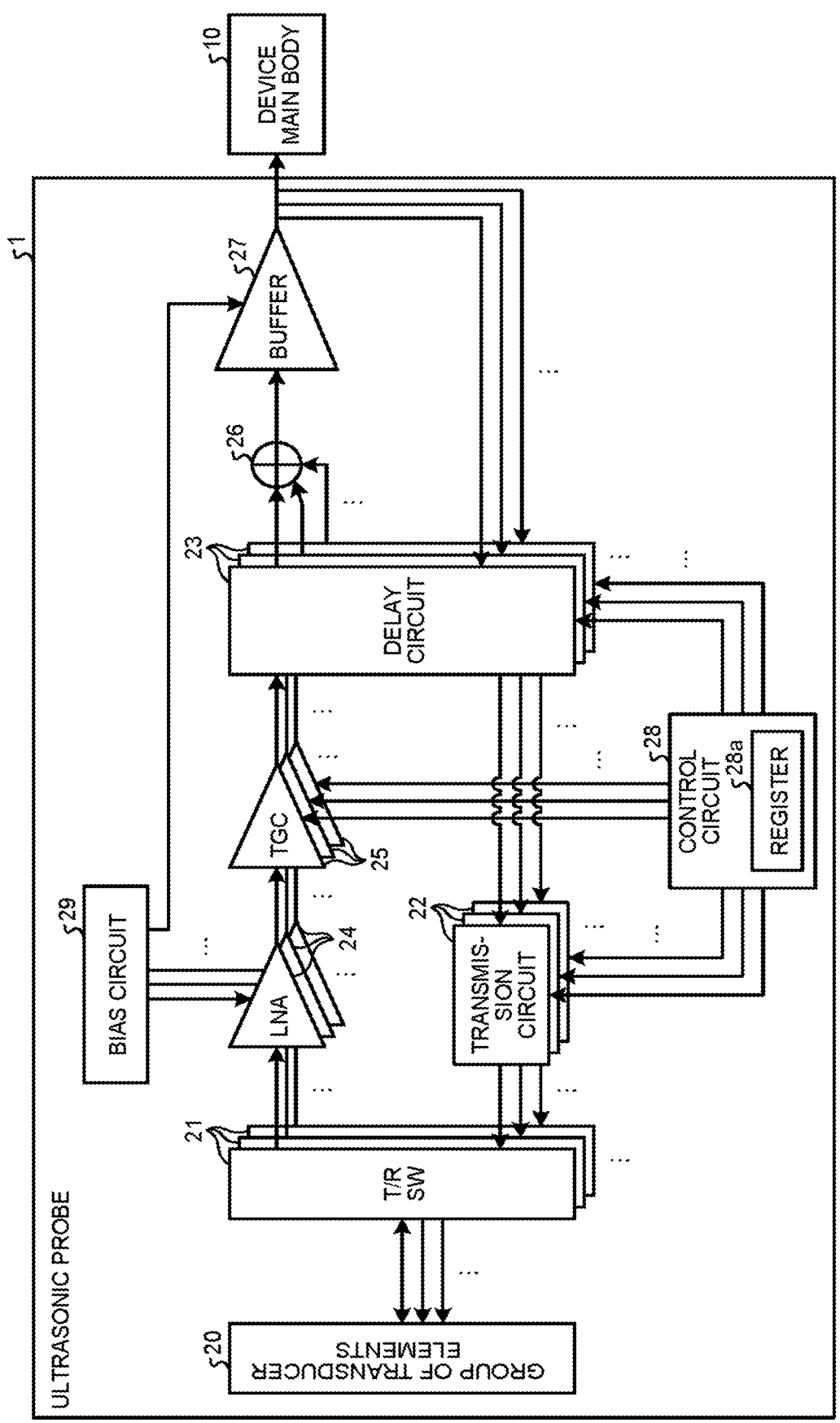
FIG. 3 is a diagram for explaining a configuration example of an ultrasonic probe according to the embodiment.

Next, with reference to FIG. 3, the following describes a configuration example of the ultrasonic probe 1 according to the embodiment. FIG. 3 is a diagram for explaining a configuration example of the ultrasonic probe 1 according to the embodiment. The configuration illustrated in FIG. 3 is a configuration example corresponding to one sub-array 20b except the group of transducer element 20.

As illustrated in the example of FIG. 3, the ultrasonic probe 1 includes, for one sub-array 20b, twenty-four transmission/reception switches (T/R SWs) 21, twenty-four transmission circuits 22, twenty-four delay circuits 23, twenty-four low noise amplifiers (LNAs) 24, twenty-four time gain controllers (TGCs) 25, an adder 26, a buffer 27, the control circuit 28, and a bias circuit. The ultrasonic probe 1 includes the electronic circuits illustrated in the example of FIG. 3 for each of all the sub-arrays 20b (in the example of FIG. 2, forty-two sub-arrays 20b) except the group of transducer elements 20 that is two-dimensionally arranged and constitutes the main array 20a.

In the embodiment, one channel is assigned to one transducer element 20c, and the transmission/reception switch 21, the transmission circuit 22, the delay circuit 23, the low noise amplifier 24, and the time gain controller 25 are provided for each channel. The adder 26, the buffer 27, the control circuit 28, and the bias circuit 29 are provided for each one of the sub-arrays 20b, not for each channel.

The transmission/reception switch 21 has a function of transmitting the drive signal output from the transmission circuit 22 to the transducer element 20c. The transmission/reception switch 21 also has a function of outputting the echo signal transmitted from the transducer element 20c to the low noise amplifier 24. The transmission/reception switch 21 is an example of a first electronic circuit, and the function of the transmission/reception switch 21 is an example of a first function.

The delay circuit 23 has a function of performing predetermined delay processing on the drive signal output from the device main body 10, and outputting the drive signal on which the predetermined delay processing is performed to the transmission circuit 22. For example, the delay circuit 23 is controlled by the control circuit 28 to perform delay processing of giving, to the drive signal supplied from the device main body 10, a delay amount for each transducer element 20c required for converging the ultrasonic waves generated from the transducer element 20c into a beam and determining transmission directivity. In this case, the delay amount given to the drive signal is indicated by a control signal output from the control circuit 28. The delay circuit 23 is an example of the first electronic circuit, and the function of the delay circuit 23 is an example of the first function.

The transmission circuit 22 has a function of supplying the drive signal to the corresponding transducer element 20c among the transducer elements 20c constituting the group of transducer elements 20 by outputting, to the transmission/reception switch 21, the drive signal output from the delay circuit 23. The transmission circuit 22 amplifies or attenuates the drive signal output from the delay circuit 23 so that the amplitude indicated by the control signal output from the control circuit 28 is obtained, and outputs the drive signal the amplitude of which is adjusted to the transducer element 20c. The transmission circuit 22 is an example of the first electronic circuit, and the function of the transmission circuit 22 is an example of the first function.

The low noise amplifier 24 is an amplifier (amp) in which the gain can be changed. In this case, the gain means an amplification factor for increasing the amplitude of the input echo signal. That is, the echo signal is largely amplified as the gain increases, and the echo signal is slightly amplified as the gain reduces.

The low noise amplifier 24 has a function of receiving the echo signal from the transducer element 20c via the transmission/reception switch 21, amplifying the received echo signal with a preset gain, and outputting the amplified echo signal to the time gain controller 25. The low noise amplifier 24 is an example of the first electronic circuit, and the function of the low noise amplifier 24 is an example of the first function.

The time gain controller 25 includes a storage unit such as a memory. In the storage unit, a plurality of kinds of functions in which the gain corresponds to an elapsed time after the ultrasonic waves are transmitted are pre-stored. When receiving the control signal output from the control circuit 28, the time gain controller 25 selects a function indicated by the received control signal from among the functions stored in the storage unit. When receiving the echo signal transmitted from the low noise amplifier 24, the time gain controller 25 changes the gain corresponding the elapsed time after the transmission of the ultrasonic waves using the selected function, and amplifies the echo signal. The time gain controller 25 then outputs the amplified echo signal to the delay circuit 23. Thus, the time gain controller 25 has a function of dynamically chancing the gain, amplifying the echo signal, and outputting the echo signal to the delay circuit 23.

Through the amplification performed by the time gain controller 25, all of the echo signals ranging from the echo signal due to reflection from a shallow portion to the echo signal due to reflection from a deep portion are adjusted to have the same amplitude.

The time gain controller 25 is an example of the first electronic circuit, and the function of the time gain controller 25 is an example of the first function. The time gain controller 25 is not necessarily provided. When the time gain controller 25 is not provided, the low noise amplifier 24 may have the function of the time gain controller 25.

In addition to the functions described above, the delay circuit 23 also has a function of performing, when receiving the echo signal output from the time gain controller 25, delay processing for giving a delay amount required for determining reception directivity on the received echo signal, and outputting the echo signal on which delay processing is performed to the adder 26. In this case, the delay amount given to the echo signal is the delay amount indicated by the control signal output from the control circuit 28.

The adder 26 has a function of performing addition processing of adding up the echo signals output from the delay circuits 23 corresponding to the transducer elements 20c that are obtained by excluding a disabled transducer element (described later) from all of the transducer elements 20c constituting the sub-array 20b corresponding to the adder 26, and outputting the echo signals on which the addition processing is performed to the device main body 10 via the buffer 27. Through the addition processing performed by the adder 26 using the echo signal, a reflection component from a direction corresponding to the reception directivity of the echo signal is emphasized. The adder 26 is an example of a second electronic circuit, and the function of the adder 26 is an example of a second function that different from the first function. A purpose of the addition processing is the same as that of the reception beam former included in the transmission/reception unit 11 described above. The addition processing is performed for channels in the sub-array 20b, so that this function in the ultrasonic probe 1 may be referred to as a sub-array beam former.

The control circuit 28 controls the operations of the transmission circuit 22, the delay circuit 23, and the time gain controller 25. For example, the control circuit 28 has an input function of inputting the control signal to the transmission circuit 22, the delay circuit 23, and the time gain controller 25. The control circuit 28 also has a control function of controlling the transmission circuit 22, the delay circuit 23, and the time gain controller 25 by inputting the control signal. Thus, the input function includes the control function.

For example, the control circuit 23 includes a register 28a. When receiving the amplitude value of the drive signal output from each transmission circuit 22, the amplitude value being output from the control unit 17 via the transmission/reception unit 11, the control circuit 28 stores the received amplitude value of the drive signal output from each transmission circuit 22 in the register 28a. When receiving the delay amount of the drive signal corresponding to each delay circuit 23 output from the control unit 17 via the transmission/reception unit 11, the control circuit 28 stores the received delay amount of the drive signal corresponding to each delay circuit 23 in the register 28a. When receiving the delay amount of the echo signal corresponding to each delay circuit 23 output from the control unit 17 via the transmission/reception unit 11, the control circuit 28 stores the received delay amount of the echo signal corresponding to each delay circuit 23 in the register 28a. When receiving the identifier for identifying the function used for time gain control in each time gain controller 25 output from the control unit 17 via the transmission/reception unit 11, the control circuit 28 stores each of received identifiers corresponding to each time gain controller 25 in the register 28a.

That is, the control circuit has a register function of holding the amplitude value that is control data for the transmission circuit 22. The control circuit 28 also has a register function of holding the delay amount of the drive signal and the delay amount of the echo signal that are pieces of control data for the delay circuit 23. The control circuit 28 also has a register function of holding the identifier that is a piece of control data for the time gain controller 25. These register functions are included in the control function.

The control circuit 28 acquires the amplitude value of the drive signal output from each transmission circuit 22 stored in the register 28a. The control circuit 28 then outputs the control signal indicating the corresponding amplitude value to each transmission circuit 22. Accordingly, each transmission circuit 22 amplifies or attenuates the drive signal output from the delay circuit 23 so that the amplitude indicated by the control signal output from the control circuit 28 is obtained, and outputs the drive signal the amplitude of which is adjusted to the transducer element 20c. Thus, the control circuit 28 has, as part of the control function, a function of controlling the amplitude of the drive signal for driving the transducer element 20c. That is, the control function includes a function of controlling the amplitude for driving the transducer element 20c.

The control circuit 28 acquires the delay amount of the drive signal corresponding to each delay circuit 23 stored in the register 28a. The control circuit 28 then outputs the control signal indicating the delay amount of the corresponding drive signal to each delay circuit 23. Accordingly, each delay circuit 23 performs delay processing of giving the drive signal output from the device main body 10 the delay amount indicated by the control signal output from the control circuit 28, and outputs the drive signal which delay processing is performed to the transmission circuit 22. Thus, the control circuit 28 has, as part of the control function, a function of controlling the delay amount of the drive signal for driving the transducer element 20c. That is, the control function includes a function of controlling the delay amount of the drive signal for driving the transducer element 20c.

The control circuit 28 acquires the delay amount of the echo signal corresponding to each delay circuit 23 stored in the register 28a. The control circuit 28 then outputs the control signal indicating the delay amount of the corresponding echo signal to each delay circuit 23. Accordingly, each delay circuit 23 performs delay processing of giving the echo signal output from the time gain controller 25 the delay amount indicated by the control signal output from the control circuit 28, and outputs the echo signal on which delay processing is performed to the adder 26. Thus, the control circuit 28 has, as part of the control function, a function of controlling the delay amount of the echo signal generated by the transducer element 20c. That is, the control function includes a function of controlling the delay amount of the echo signal.

The control circuit 28 acquires each identifier corresponding to each time gain controller 25 stored in the register 28a. The control circuit 28 then outputs the control signal indicating the corresponding identifier to each time gain controller 25. Accordingly, the time gain controller 25 selects, from among the functions stored in the storage unit, the function specified with the identifier indicated by the control signal transmitted from the control circuit 28. When receiving the echo signal transmitted from the low noise amplifier 24, the time gain controller 25 changes the gain corresponding to the elapsed time using the selected function, and amplifies the echo signal. Thus, the control circuit 28 has, as part of the control function, a gain control function of dynamically controlling the gain of the time gain controller 25. That is, the control function includes the gain control function of dynamically controlling the gain of the time gain controller 25.

The control circuit 28 is an example of the second electronic circuit, and the function of the control circuit 28 is an example of the second function.

The bias circuit 29 has a function of supplying a bias current to each low noise amplifier 24 and the buffer 27 to cause each low noise amplifier 24 and the buffer 27 to be operated. The bias circuit 29 is an example of the second electronic circuit, and the function of the bias circuit 29 is an example of the second function.

The transmission/reception switch 11, the transmission circuit 22, the delay circuit 23, the low noise amplifier 24, the time gain controller 25, the adder 26, the buffer 27, the control circuit 28, and the bias circuit 29 may be arranged on the opposite side of an ultrasonic wave emitting surface of the transducer element 20c, that is, a back surface of the transducer element 20c. In such a case, the transmission/reception switch 21, the transmission circuit 22, the delay circuit 23, the low noise amplifier 24, and the time gain controller 25, required for each one of the transducer elements 20, may be arranged at a position opposed to each transducer element 20c.

When the components are arranged as described above, the transmission/reception switch 21, the transmission circuit 22, the delay circuit 23, the low noise amplifier 24, and the time gain controller 25 are already arranged at the position opposed to each transducer element 20c, so that there may be no space for arranging the adder 6, the buffer 27, the control circuit 28, and the bias circuit 29 in some cases.

Thus, in such a case, the adder 26, the buffer 27, the control circuit 28, and the bias circuit 29 may be arranged at a position outside of the position opposed to each transducer element 20c. However, when the adder 26, the buffer 27, the control circuit 28, and the bias circuit 29 are arranged at the position outside of the position opposed to each transducer element 20c, an area of the transducer element 20c and a region in which the electronic circuits including the transmission/reception switch 21, the transmission circuit 22, the delay circuit 23, the low noise amplifier 24, the time gain controller 25, the adder 26, the buffer 27, the control circuit 28, and the bias circuit 29 are arranged may increase. When the area of the region in which the electronic circuits are arranged increases, an area of a surrounding portion of an acoustic radiation surface constituted of the transducer elements 20c in the ultrasonic probe 1 may increase.

When the area of the surrounding portion of the acoustic radiation surface increases, an area of a contact surface between the ultrasonic probe 1 and the subject P may increase. In this case, when the area of the contact surface between the ultrasonic probe 1 and the subject P is large, for example, it may be difficult to cause the ultrasonic waves to be incident into the subject P when the ultrasonic waves are caused to enter from a relatively narrow gap between ribs of the subject P.

Accordingly, as described below, the ultrasonic probe 1 applied to the ultrasonic diagnostic device 100 according to the embodiment is configured to prevent the area of the contact surface with the subject P from being increased.

Figure 4:
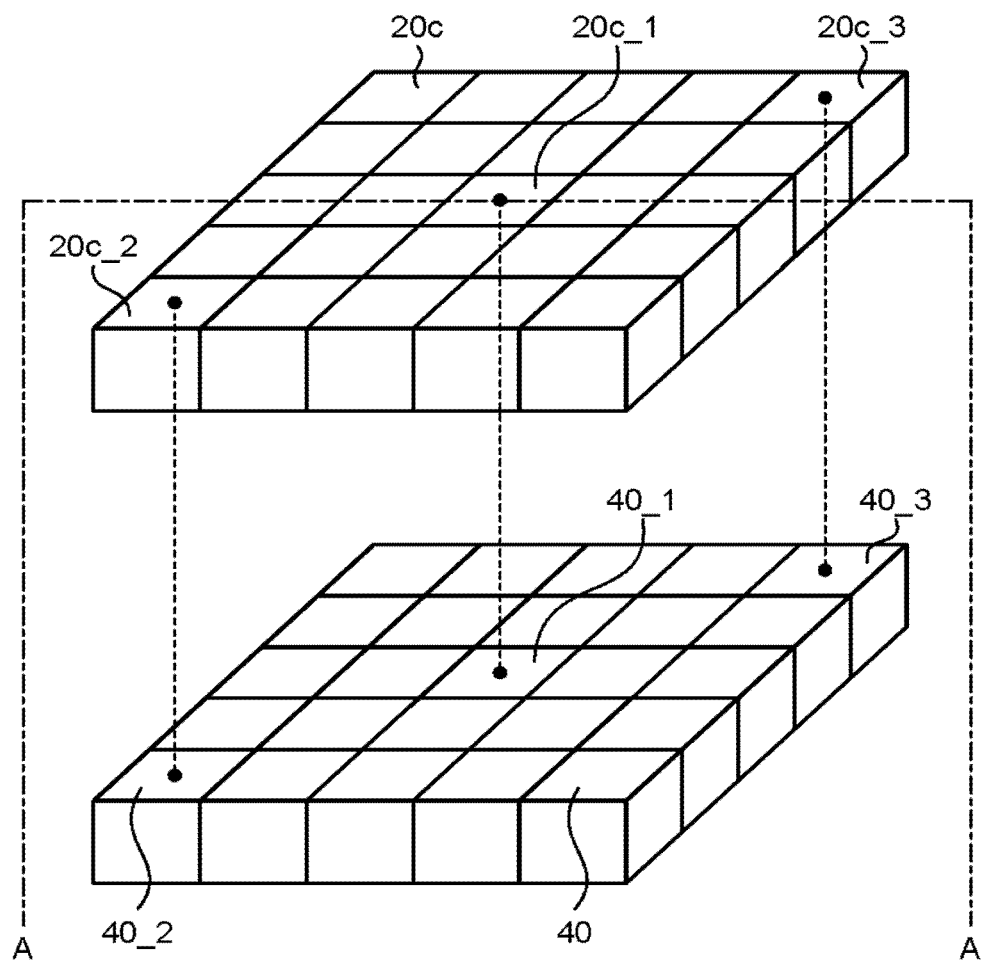
FIG. 4 is a diagram illustrating an example of a positional relation between the transducer element and a region in which each of electronic circuits including a transmission/reception switch, a transmission circuit, a delay circuit, a low noise amplifier, a time gain controller, an adder, a buffer, a control circuit, and a bias circuit is arranged.

FIG. 4 is a diagram illustrating an example of a positional relation between the transducer element 20c and the region in which each of the electronic circuits including the transmission/reception switch 21, the transmission circuit 22, the delay circuit 23, the low noise amplifier 24, the time gain controller 25, the adder 26, the buffer 27, the control circuit 28, and the bias circuit 29 is arranged. FIG. 4 illustrates an example of the positional relation between the transducer elements 20c corresponding to one sub-array 20b and regions in which each of the electronic circuits is arranged.

As illustrated in the example of FIG. 4, the group of transducer elements 20 is arranged in substantially a grid, and a plurality of electronic circuit are arranged in substantially a grid to correspond to the arrangement of a plurality of transducer elements 20c constituting the sub-array 20b.

As illustrated in the example of FIG. 4, each of twenty-five regions 40 in which the electronic circuits are arranged is present at a position on the back surface side of the transducer element 20c, the position being opposed to each of the twenty-five transducer elements 20c. For example, a region 40_1 positioned at the center of the twenty-five regions 40 is opposed to a transducer element 20c_1 positioned at the center of one sub-array 20b. A region 40_2 is present at a position opposed to a transducer element 20c_2. A region 40_3 is present a position opposed to a transducer element 20c_3.

The region 40 illustrated in the example of FIG. 4 is schematic. Actually, lines for partitioning the regions 40 are not present. In the example of FIG. 4, the reference numeral "20c" is given to only one transducer element, and the reference numeral "20c" is not given to the other transducer elements. Similarly, in the example of FIG. 4, the reference numeral "40" is given to only one region, and the reference numeral "40" is not given to the other regions.

Figure 5A:
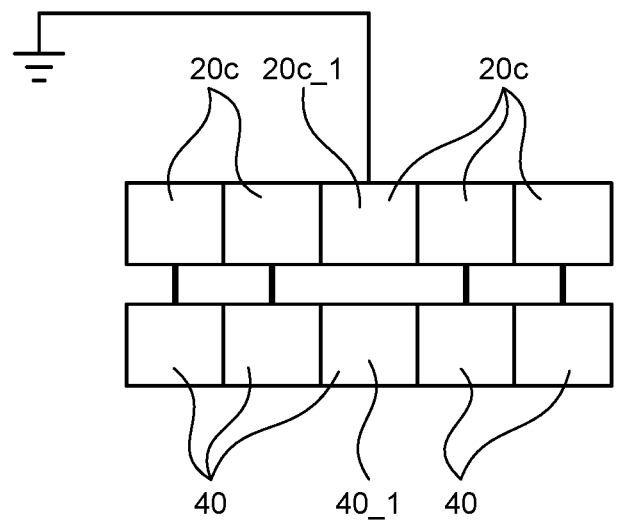
FIG. 5A is a cross-sectional view along a cutting line A-A in FIG. 4 in a case in which a sub-array corresponding to the transducer elements illustrated in the example of FIG. 4 is not positioned at an end of a main array.

FIG. 5A is a cross-sectional view along a cutting line A-A in FIG. 4 in a case in which the sub-array 20b corresponding to the transducer elements 20c illustrated in the example of FIG. 4 is not positioned at an end of the main array 20a. Elongated bold black lines illustrated in FIG. 5A represent that the transducer elements 20c are electrically connected to the electronic circuits arranged in the region 40. Thus, as illustrated in FIG. 5A, the transducer elements 20c other than the transducer element 20c_1 are electrically connected to the electronic circuits arranged at the opposed position.

The transducer element 20c_1 is grounded instead of being connected to the electric circuits. Accordingly, the transducer element 20c_1 does not have a function of transmitting and receiving ultrasonic waves. Thus, the function of transmitting and receiving ultrasonic waves is disabled, so that the transducer element 20c_1 is also referred to as the disabled transducer element.

Figure 5B:
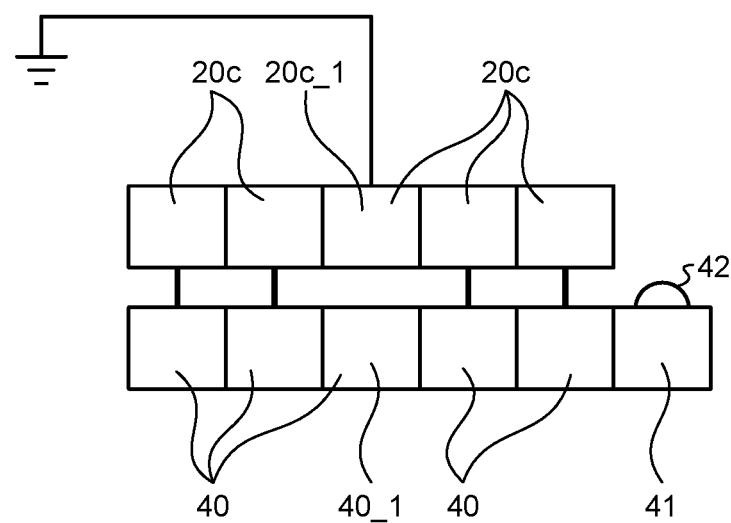
FIG. 5B is a cross-sectional view along the cutting line A-A in FIG. 4 in a case in which the sub-array corresponding to the transducer elements illustrated in the example of FIG. 4 is positioned at the end of the main array.

FIG. 5B is a cross-sectional view along the cutting line A-A in FIG. 4 in a case in which the sub-array 20b corresponding to the transducer elements 20c illustrated in the example of FIG. 4 is positioned at the end of the main array 20a. Elongated bold black lines illustrated in FIG. 5B also represent that the transducer elements 20c are electrically connected to the electronic circuits arranged in the region 40. Thus, as illustrated in FIG. 5B, the transducer elements 20c other than the transducer element 20c_1 are electrically connected to the electronic circuits arranged at the opposed position. The transducer element 20c_1 is grounded similarly to the case illustrated in the example of FIG. 5A.

When the sub-array 20b is positioned at the end of the main array 20a, an outer circumference region 41 is present as illustrated in FIG. 5B. In the outer circumference region 41, a pad 42 is arranged to electrically connect the device main body 10 to the delay circuit 23, the buffer 27, and the control circuit 28 of the ultrasonic probe 1. The pad 42 is electrically connected to the device main body 10, the delay circuit 23, the buffer 27, and the control circuit 28. With the configuration, the drive signal is output from the device main body 10 to the delay circuit 23, the echo signal output from the buffer 27 to the device main body 10, and the control data such as the amplitude value of the drive signal, the delay amount of the drive signal, the delay amount of the echo signal, and the identifier for identifying the function is output from the device main body 10 to the control circuit 28.

In the example of FIG. 5A and FIG. 5B, in order to pick up signals, for example, substrate or flexible printed circuits (FPCs) may be arranged between the transducer element 20c and the electronic circuits arranged in the region 40. Accordingly, the transducer element 20c is electrically connected to the electronic circuits arranged in the region 40 via the substrates or the flexible printed circuits for picking up the signals.

Figure 6:
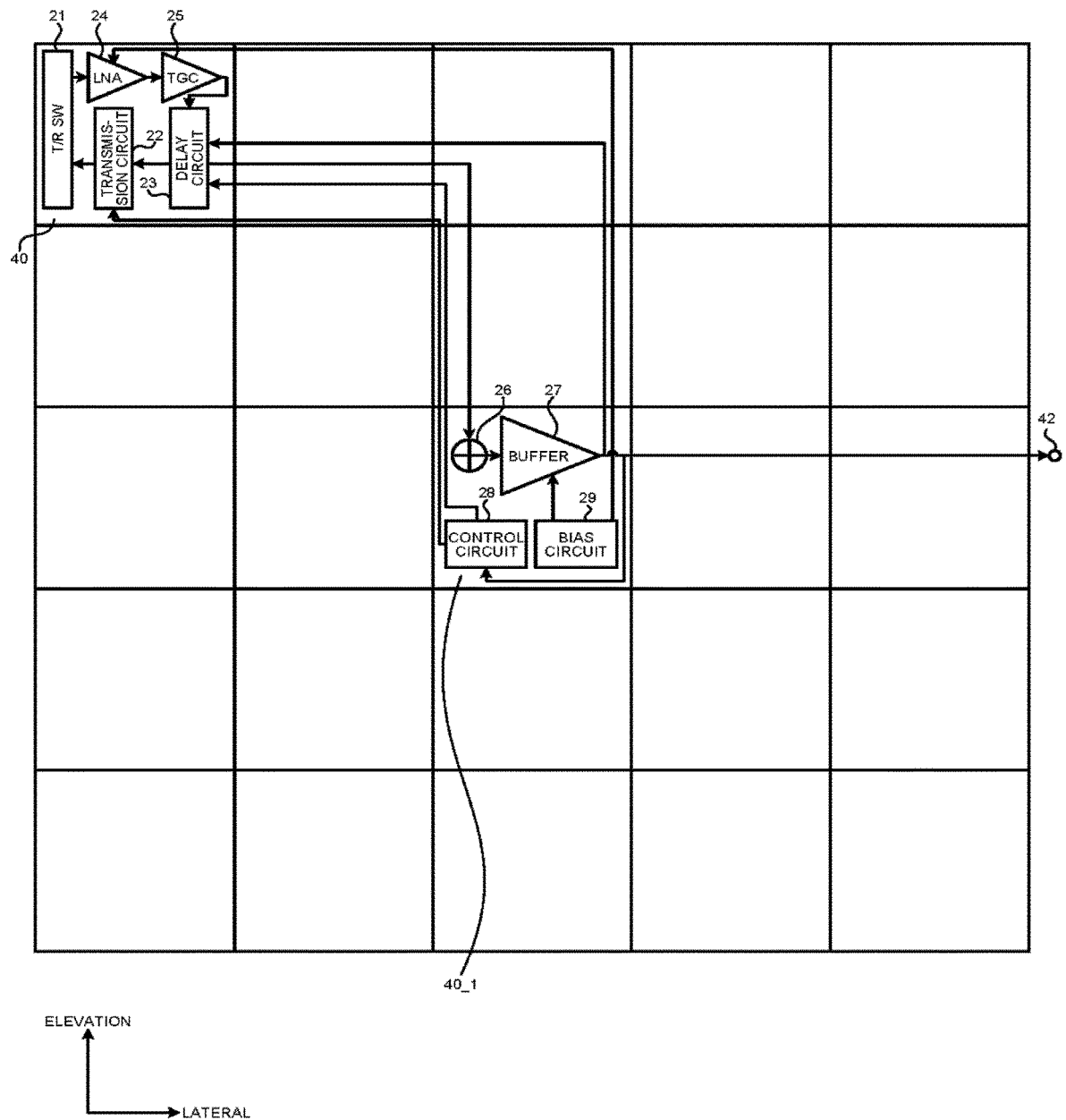
FIG. 6 is a diagram illustrating an example of an arrangement of the electronic circuits corresponding to one sub-array.

FIG. 6 a diagram illustrating an example of the arrangement of the electronic circuits corresponding to one sub-array 20b. As illustrated in the example of FIG. 6, the adder 26, the buffer 27, the control circuit 28, and the bias circuit 29 are arranged in the region 40_1 opposed to the transducer element 20c_1 as the disabled transducer element. In each of the twenty-four regions 40 other than the region 40_1, the transmission/reception switch 21, the transmission circuit 22, the delay circuit 23, the low noise amplifier 24, and the time gain controller 25 are arranged. FIG. 6 illustrates an example in which the transmission/reception switch 21, the transmission circuit 22, the delay circuit 23, the low noise amplifier 24, and the time gain controller 25 are arranged in one region 40, and does not illustrate the transmission/reception switch 21, the transmission circuit 22, the delay circuit 23, the low noise amplifier 24, and the time gain controller 25 arranged in each f the other twenty-three regions 40.

As illustrated in the example of FIG. 6, the electronic circuits are two-dimensionally arranged corresponding to the arrangement of the transducer elements 20c constituting the sub-array 20b.

As illustrated in the example of FIG. 6, the electronic circuits including the transmission/reception switch 21, the transmission circuit 22, the delay circuit 23, the low noise amplifier 24, the time gain controller 25, the adder 26, the buffer 27, the control circuit 28, and the bias circuit 29 are arranged to fit within the back surface side of the group of transducer elements 20. Thus, the area of the surrounding portion of the acoustic radiation surface constituted of the transducer elements 20c in the ultrasonic probe 1 is not required to be increased. Accordingly, the ultrasonic probe 1 can prevent the area of the contact surface with the subject P from being increased.

As described above, the area of the contact surface with the subject P is prevented from being increased, so that the ultrasonic probe 1 can easily cause the ultrasonic waves to be incident into the subject P when causing the ultrasonic waves to enter from a relatively narrow gap between the ribs of the subject P, for example.

The adder 26, the buffer 27, the control circuit 28, and the bias circuit 29, arranged for each one of the sub-arrays 20b, are arranged corresponding to the transducer element 20c positioned at the center of the sub-array 20b. Such an arrangement can prevent wiring between the adder 26, the buffer 27, the control circuit 28, and the bias circuit 29, and the other electronic circuits from being complicated as compared with a case in which the adder 26, the buffer 27, the control circuit 28, and the bias circuit 29 are arranged corresponding to the transducer element 20c positioned at a place other than the center of the sub-array 20b.

In the embodiment, one disabled transducer element is present for each one of the sub-arrays 20b. However, influence of the disabled transducer element on overall acoustic performance is insignificant. As detailed above, the ultrasonic probe 1 can easily cause the ultrasonic waves to be incident into the subject P when causing the ultrasonic waves to enter from a relatively narrow gap between the ribs of the subject P, and the wiring can be prevented from being complicated. These effects are significant as compared with the influence of the disabled transducer element.

In the above, described is the case in which the sub-array 20b is constituted of a plurality of transducer elements 20c arranged in a grid of "5×5". In this way, when the sub-array 20b is constituted of a plurality of transducer elements 20c arranged in a grid of "odd number×odd number", the transducer element 20c positioned at the center of the sub-array 20b can be specified, so that the adder 26, the buffer 27, the control circuit 28, and the bias circuit 29 are inevitably arranged at the center of the region in which the other electronic circuits are arranged. This configuration can efficiently prevent the wiring from being complicated.

Figure 7:
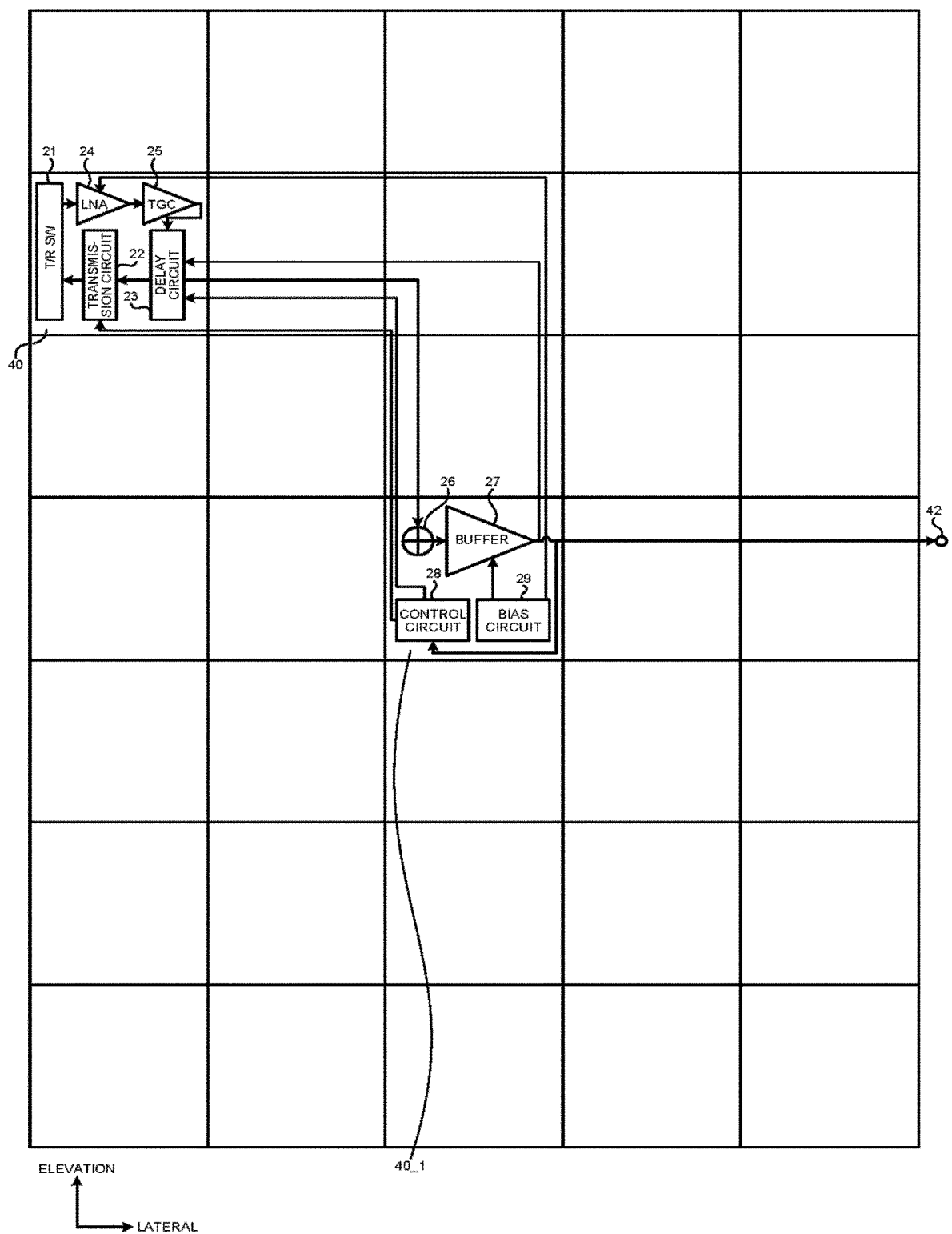
FIG. 7 is a diagram illustrating another example of the arrangement of the electronic circuits corresponding to one sub-array.

Alternatively, the sub-array 20b may be constituted of a plurality of transducer elements 20c arranged in a grid of "N×M" (each of N and M is an arbitrary natural number). FIG. 7 is a diagram illustrating another example of the arrangement of the electronic circuits corresponding to one sub-array 20b. For example, as illustrated in the example of FIG. 7, the sub-array 20b may be constituted of a plurality of transducer elements 20c arranged in a grid of "5×7". Also in this case, the sub-array 20b is constituted of a plurality of transducer elements 20c arranged in a grid of "odd number×odd number", so that the wiring can be efficiently prevented from being complicated.

The adder 26, the buffer 27, the control circuit 28, and the bias circuit 29 may be arranged corresponding to the transducer element 20c present at a surrounding portion of the transducer element 20c positioned at the center of the sub-array 20b, instead of being arranged corresponding to the transducer element 20c positioned at the center of the sub-array 20b. For example, the adder 26, the buffer 27, the control circuit 28, and the bias circuit 29 may be arranged corresponding to the transducer element 20c adjacent to the transducer element 20c positioned at the center of the sub-array 20b. That is, the adder 26, the buffer 27, the control circuit 28, and the bias circuit 29 may be arranged corresponding to the transducer element 20c positioned at substantially the center of the sub-array 20b.

When the sub-array 20b is constituted of a plurality of transducer elements 20c arranged in a grid of "odd number×even number", "even number×odd number", and "even number×even number", the transducer element 20c positioned at the center of the sub-array 20b cannot be uniquely specified. Accordingly, in such a case, the adder 26, the buffer 27, the control circuit 28, and the bias circuit 29 may be arranged corresponding to the transducer element 20c positioned at substantially the center of the sub-array 20b.

Figure 8:
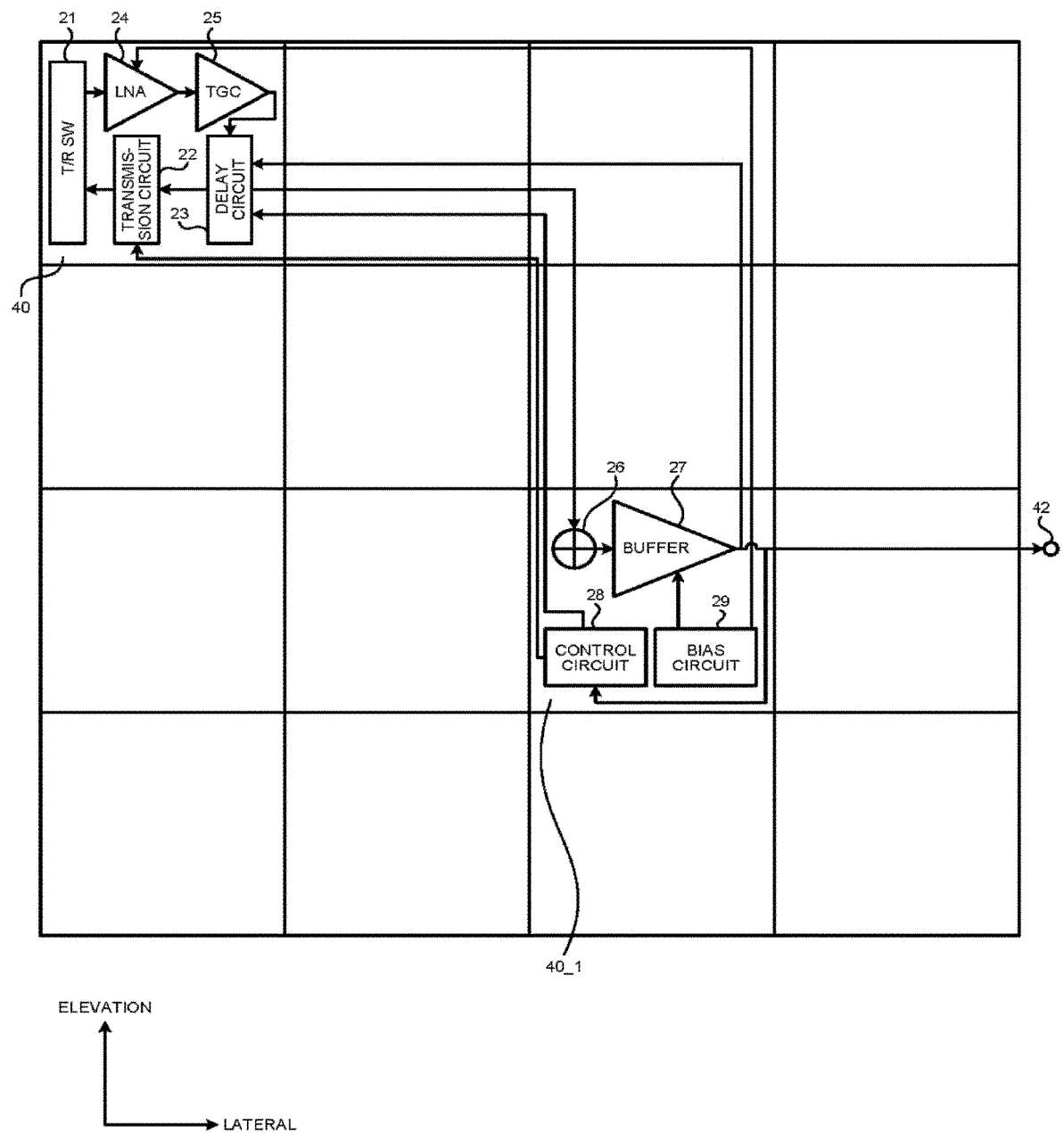
FIG. 8 is a diagram illustrating yet another example of the arrangement of the electronic circuits corresponding to one sub-array.

FIG. 8 is a diagram illustrating yet another example of the arrangement of the electronic circuits corresponding to one sub-array 20b. As illustrated in the example of FIG. 8, when the sub-array 20b is constituted of a plurality of transducer elements 20c arranged in a grid of "even number×even number" ("4×4"), the transducer element 20c positioned at the center of the sub-array 20b cannot be uniquely specified. Accordingly, in such case, the adder 26, the buffer 27, the control circuit 28, and the bias circuit 29 may be arranged corresponding to any of the four transducer elements 20c positioned at substantially the center of the sub-array 20b.

The adder 26, the buffer 27, the control circuit 28, and the bias circuit 29 may be arranged corresponding to the transducer element 20c that is not positioned at the center or substantially the center of the sub-array 20b, instead of being arranged corresponding to the transducer element 20c positioned at the center or substantially the center of the sub-array 20b.

In the above, described is the case in which a plurality of sub-arrays 20b are two-dimensionally arranged. Alternatively, the sub-arrays 20b may be arranged in a column. That is, the sub-arrays 20b may be one-dimensionally arranged. In this case, the electronic circuits described above are also one-dimensionally arranged.

With the ultrasonic probe and the ultrasonic diagnostic device according to at least one embodiment described above, the area of the contact surface with the subject P can be prevented from being increased.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic probe comprising:
a group of transducer elements two-dimensionally arranged and constituting a main array that is divided into a plurality of sub-arrays; and
a plurality of electronic circuits arranged corresponding to an arrangement of the transducer elements constituting the sub-array, wherein
at least one of the electronic circuits is a first electronic circuit having a first function,
at least one of the electronic circuits is a second electronic circuit having a second function different from the first function, and
the second electronic circuit is arranged for each one of the sub-arrays, the second electronic circuit being opposed to a transducer element, among the transducer elements, which does not transmit and receive ultrasonic waves, and the second electronic circuit being arranged so as to be included in an area of the transducer element, wherein
the second electronic circuit is arranged corresponding to a transducer element positioned at substantially a center of the sub-array.

2. The ultrasonic probe according to claim 1, wherein
the group of transducer elements is arranged in a grid, and
the electronic circuits are arranged in a grid, each of the electronic circuits corresponding to one of the transducer elements constituting the sub-array.

3. The ultrasonic probe according to claim 1, wherein the first electronic circuit has, as at least part of the first function, a function of performing delay processing on a drive signal for driving the transducer elements and outputting the drive signal.

4. The ultrasonic probe according to claim 1, wherein the first electronic circuit has, as at least part of the first function, a function of performing predetermined processing on an echo signal generated by the transducer elements and outputting the echo signal.

5. The ultrasonic probe according to claim 4, wherein the predetermined processing includes delay processing on the echo signal.

6. The ultrasonic probe according to claim 1, wherein the second electronic circuit has, as at least part of the second function, a function of performing processing on a signal output from the first electronic circuit.

7. The ultrasonic probe according to claim 6, wherein the processing on the signal output from the first electronic circuit includes addition processing using the signal output from the first electronic circuit.

8. The ultrasonic probe according to claim 1, wherein the second electronic circuit has, as at least part of the second function, an input function for the first electronic circuit.

9. The ultrasonic probe according to claim 8, wherein the input function includes a control function of controlling the first electronic circuit.

10. The ultrasonic probe according to claim 9, wherein the control function includes a register function of holding control data for the first electronic circuit.

11. The ultrasonic probe according to claim 9, wherein the control function includes a function of controlling a delay amount of a drive signal for driving the transducer elements.

12. The ultrasonic probe according to claim 9, wherein the control function includes a function of controlling amplitude of a drive signal for driving the transducer elements.

13. The ultrasonic probe according to claim 9, wherein the control function includes a gain control function of dynamically controlling a gain of the first electronic circuit.

14. The ultrasonic probe according to claim 1, wherein the sub-array is constituted of the transducer elements arranged in a grid of M×N (each of M and N is an odd number).

15. The ultrasonic probe according to claim 1, wherein the sub-array is constituted of the transducer elements arranged in a grid of N×N (N is an odd number).

16. The ultrasonic probe according to claim 1, wherein, among the transducer elements, a transducer element corresponding to the arrangement of the first electronic circuit is connected to the corresponding first electronic circuit, and the transducer element opposed to the arrangement of the second electronic circuit is grounded instead of being connected to the first electronic circuit.

17. The ultrasonic probe according to claim 1, wherein the electronic circuits are arranged as a layer of circuits disposed in a grid having M×N areas, the first and second electronic circuits each being contained in one of the areas and being opposed to one of the transducer elements.

18. An ultrasonic diagnostic device comprising:
image generation circuitry configured to generate an ultrasonic image based on an output from an ultrasonic probe, the ultrasonic probe including a group of transducer elements two-dimensionally arranged and constituting a main array that is divided into a plurality of sub-arrays and a plurality of electronic circuits arranged corresponding to an arrangement of the transducer elements constituting the sub-array, at least one of the electronic circuits being a first electronic circuit having a first function, at least one of the electronic circuits being a second electronic circuit having a second function different from the first function, and the second electronic circuit being arranged for each one of the sub-arrays, the second electronic circuit being opposed to a transducer element, among the transducer elements, which does not transmit and receive ultrasonic waves, and the second electronic circuit being arranged so as to be included in an area of the transducer element; and
control circuitry configured to cause a display to display the ultrasonic image, wherein
the second electronic circuit is arranged corresponding to a transducer element positioned at substantially a center of the sub-array.

19. The ultrasonic diagnosis device according to claim 18, wherein the electronic circuits are arranged as a layer of circuits disposed in a grid having M×N areas, the first and second electronic circuits each being contained in one of the areas and being opposed to one of the transducer elements.

* * * * *